United States Patent [19]

Stern et al.

[11] Patent Number: 5,714,714
[45] Date of Patent: Feb. 3, 1998

[54] PROCESS FOR PREPARING AMMONIUM DINITRAMIDE

[75] Inventors: Alfred G. Stern, Landover; William M. Koppes; Michael E. Sitzmann, both of Adelphi; Lori A. Nock, Woodlawn; Donna M. Cason-Smith, Columbia, all of Md.

[73] Assignee: The United States of America as represented by the Secretary of the Navy, Washington, D.C.

[21] Appl. No.: 990,116

[22] Filed: Oct. 15, 1992

[51] Int. Cl.[6] .................................................. D03D 23/00
[52] U.S. Cl. .......................... 149/109.6; 149/61; 149/122; 264/3.1
[58] Field of Search ................... 269/3.1, 3.5; 149/45, 149/61, 112, 122, 109.6

[56] References Cited

U.S. PATENT DOCUMENTS 3,390,183  6/1968  Frankel et al. ................. 149/88 X
3,634,154  1/1972  Burdette ........................ 149/36 X
3,716,315  2/1973  King .............................. 264/3.5 X
5,198,204  3/1993  Bottaro et al. ................. 423/385

*Primary Examiner*—Peter A. Nelson
*Attorney, Agent, or Firm*—John Forrest; Roger D. Johnson

[57] ABSTRACT

A process for preparing ammonium dinitramide by:

(1) nitrating either ethyl carbamate or methyl carbamate to form the corresponding mononitrate compound, ethyl N-nitrocarbamate or methyl N-nitrocarbamate;

(2) reacting the N-nitrocarbamate with ammonia under anhydrous conditions to produce the corresponding ammonium salt, ammonium ethyl N-nitrocarbamate or ammonium methyl N-nitrocarbamate;

(3) nitrating the ammonium salt and then treating the reaction mixture with ammonia to produce ammonium dinitramide, ammonium nitrate, and regenerate the original ethyl carbamate or methyl carbamate compound.

8 Claims, No Drawings

PROCESS FOR PREPARING AMMONIUM DINITRAMIDE

BACKGROUND OF THE INVENTION

This invention relates to energetic compounds and more particularly to energetic inorganic nitro compounds.

Ammonium dinitramide (ADN) was first synthesized by R. J. Schmitt and J. C. Bottaro of SRI International. Later ADN was prepared by the nitration of ammonia with $N_2O_5$, $NO_2BF_4$, and $(NO_2)HS_2O_7$. All these methods suffer from low yields and require costly, time consuming purification steps.

SUMMARY OF THE INVENTION

An object of this invention is to provide a new method of producing ammonium dinitramide.

Another object of this invention is to provide a method of producing ammonium dinitramide in greater yield than in previous methods.

A further object of this invention is to provide a less expensive method of producing ammonium dinitramide.

Yet another object of this invention is to provide a method of producing ammonium dinitramide with an easier purification method.

These and other objectives of this inventon are accomplished by providing a process for producing ammonium dinitrimide comprising the following steps in order:

(1) nitrating a compound of the formula Z—$NH_2$ to form a compound of the formula Z—$NHNO_2$;

(2) reacting the compound Z—$NHNO_2$ with ammonia under anhydrous conditions to produce a salt of the formula Z—$NNO_2^-NH_4^+$;

(3) treating the salt Z—$NNO_2^-NH_4^+$ with a nitrating agent, and then with ammonia to produce ammonium dinitramide, ammonium nitrate, and regenerate the compound Z—$NH_2$, and (4) isolating the product ammonium dinitramide; wherein Z is —$COOCH_2CH_3$, or —$COOCH_3$.

DETAILED DESCRIPTION OF THE PREFERRED EMBODIMENT

The process of this invention produces ammonium dinitramide by using a substrate compound that functions as a protected form of ammonia. It allows for introduction of two nitro groups on the ammonia nitrogen (in high yield) followed by treatment with ammonia to give ammonium dinitramide, ammonium nitrate, and regenerate starting compound.

The substrate compound may be represented by the formula Z—$NH_2$ wherein Z is preferably —$COOCH_2CH_3$, or —$COOCH_3$, and most preferably —$COOCH_2CH_3$. Specifically the substrate compound is ethyl carbamate, $CH_3CH_2OOCNH_2$, or methyl carbamate, $CH_3OOCNH_2$. The process can be summarized by the following equations

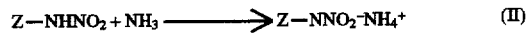

wherein Z is as defined above.

In the first step of the process (see equation I above), the substrate compound Z—$NH_2$ is nitrated in solution to form the compound of the formula Z—$NHNO_2$ wherein Z is as defined above. Specifically, ethyl carbamate or methyl carbamate is nitrated to form the corresponding mononitrate compound: ethyl N-nitrocarbamate, $CH_3CH_2OOCNHNO_2$, or methyl N-nitrocarbamate, $CH_3OOCNHNO_2$, respectively. One equivalent of nitrating agent per mole of substrate compound is used. The nitration agent is selected to preferentially produce the mononitro compound. The most preferred nitrating agent for this mononitration step is acetyl nitrate. Because acetyl nitrate is corrosive, explosive, and unstable in the pure form, acetyl nitrate is prepared and used in situ. The Merck Index warns that "acetyl nitrate will always explode when heated suddenly over 60° C." Therefore cooling is used during the initial formation of acetyl nitrate and during the initial reaction stage of acetyl nitrate with the substrate to prevent overheating. As illustrated in example 1, the acetyl nitrate may be produced by slowly adding fuming nitric acid to excess acetic anhydride with cooling to prevent overheating (temperature 10° C. or less). The reaction is $(CH_3COO)_2O+HNO_3 \rightarrow CH_3CO(ONO_2)+CH_3COOH$. The resulting product is the acetyl nitrate in a solvent mixture of the acetic acid byproduct and the excess acetic anhydride remaining after the reaction.

In this first process step each mole of substrate compound (ethyl carbamate or methyl carbamate) reacts with one equivalent of nitrating agent (e.g., acetyl nitrate) to form the N-nitro derivative. When acetyl nitrate is the nitrating agent, additional acetic acid will be formed as a byproduct (see equation (I)).

The N-nitro product is then isolated and purified. When acetyl nitrate is used, the volatiles, acetic acid and acetic anhydride, are distilled off, leaving the solid N-nitrocarbamate product, Z—$NHNO_2$. This can be purified by trituration with $CCl_4$ (as shown in example 1) to obtain rigorously pure material, or the product can be allowed to dry thoroughly and converted to its salt directly.

In the second step of the process (see equation (II) above), the N-nitro compound, Z—$NHNO_2$, is reacted with anhydrous $NH_3$ to form the ammonium salt of the formula Z—$NNO_2^-NH_4^+$, wherein Z is as defined above. Specifically, ethyl N-nitrocarbamate or methyl N-nitrocarbamate is treated with anhydrous ammonia to form the corresponding ammonium salt: ammonium ethyl N-nitrocarbamate ($CH_3CH_2OOCNNO_2^-NH_4^+$) or ammonium methyl N-nitrocarbamate ($CH_3OOCNNO_2^-NH_4^+$), respectively. The more preferred ammonium salt is ammonium ethyl N-nitrocarbamate. The ammonium salt is prepared by adding dry ammonia gas to an anhydrous solution of the ethyl or methyl N-nitrocarbamate compound under an inert atmosphere (dry nitrogen, argon, helium, etc.) with cooling to maintain the reaction mixture temperature preferably below 25° and more preferably below 20° C. In the preferred solvent or solvent mixture, the ethyl or methyl N-nitrocarbamate compound will be soluble, but the ammonium salt product will be insoluble. For instance, in example 2, ethyl N-nitrocarbamate is dissolved in an approximately 2:1 (by volume) solvent mixture of dry $CH_2Cl_2$ and dry $CH_3OH$. When dry ammonia gas is bubbled into the solution, the product ammonium ethyl N-nitrocarbamate precipitates out. Chloroform ($CHCl_3$) may be used in place of methylene chloride ($CH_2Cl_2$); however, methylene chloride is the most preferred chlorohydrocarbon solvent for this step. Similarly, ethanol may be used in place of methanol; however, methanol is the most preferred alcohol for this step.

In the third step of the process (see equation III) the ammonium N-nitrocarbamate salt, Z—$NNO_2^-NH_4^+$, is nitrated to form a proposed intermediate compound N,N-dinitrocarbamate Z—N(NO$_2$)$_2$. The intermediate compound has not been isolated or unequivically identified. Specifically, (1) ammonium ethyl N-nitrocarbamate salt, CH$_3$CH$_2$OOCNNO$_2^-$NH$_4^+$, is nitrated to form the proposed intermediate ethyl N,N-dinitrocarbamate, CH$_3$CH$_2$OOCNN(NO$_2$)$_2$, or (2) ammonium methyl N-nitrocarbamate salt, CH$_3$OOCNNO$_2^-$NH$_4^+$, is nitrated to form the proposed intermediate methyl N,N-dinitrocarbamate, CH$_3$OOCN(NO$_2$)$_2$. The ammonium N-nitrocarbamate salt Z—NNO$_2^-$ NH$_4^+$, is suspended in CH$_2$Cl$_2$ or CHCl$_3$, with CH$_2$Cl$_2$ being more preferred, and then nitrated at a temperature of preferably less than −35° C. under an inert atmosphere (nitrogen, argon, helium, neon, etc.) to produce the proposed N,N-dinitrocarbamate Z—N(NO$_2$)$_2$. The low end of the reaction temperature range is not critical, but the upper end of the range is limited by the limited stability of the intermediate product. Suitable nitration agents include preferably nitrogen pentoxide or nitronium tetrafluoroborate, with nitrogen pentoxide being preferred. This procedure is illustrated by example 4.

In the fourth process step, the intermediate N,N-dinitrocarbamate is reacted with ammonia to produce (1) the desired ammonium dinitramide product, (2) ammonium nitrate as a useful byproduct, and (3) the regenerated substrate compound Z—NH$_2$. This can be conveniently done by bubbling ammonia into the solution produced by the nitration reaction in step 3. The ammonium dinitramide and ammonium nitrate will be present as a solid precipitate mixture which can be filtered off leaving a solution which contains the regenerated substrate compound. The solvent can be evaporated leaving the substrate compound Z—NH$_2$ which can be reused. By using an appropriate solvent (such as CH$_3$C≡N) the ammonium dinitramide can be separated from the ammonium nitrate as illustrated by example 4.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1

Preparation of ethyl N-nitrocarbamate

Fuming nitric acid (389.3 g, 5.56 mol, 90%) was added dropwise to rapidly stirred acetic anhydride (1135.2 g, 11.12 mol) at 0° C. under N$_2$ (The HNO$_3$ addition rate was controlled so as not to exceed a reaction temperature of 6° C.). After the acid addition was complete, the reaction solution was warmed to 25° C. (over 15 minutes) and was allowed to stir at 25° C. for 30 minutes. The solution was then cooled to 0° C. and solid ethyl carbamate (500 g, 5.56 mol, 99%) was added (in portions) over 70 minutes, so as not to exceed a reaction temperature of 10° C. After the ethyl carbamate addition was complete, the solution was allowed to stir at 0° C. for 2 hours and was allowed to warm to 25° C. over 1 hour. The volatiles were then evaporated in vacuo (at 25° C.) to give yellow crystals (ca. 820 g) that were triturated with CCl$_4$ (500 mL), were filtered, and were washed with CCl$_4$ (500 mL). Evaporation of the filtrates and two repetitions of the CCl$_4$ purification process on the filtrate residues removed most of the acetic acid. (Note: The presence of acetic acid in CCl$_4$ greatly enhances the solubility of the product ethyl N-nitrocarbamate.) The combined crystals were then triturated with CCl$_4$ (500 mL), were filtered, and were dried under high vacuum to give colorless crystals of the product ethyl N-nitrocarbamate (554.0 g, 74%). mp 63°–66° C. (lit. 64° C.); IR (KBr) 3250 (s), 3020 (m) and 3010(m), 1755 (s), 1615 (s), 1460 (s), 1400 (s), 1330 (s), 1230 (s) 1000 (s) cm$^{-1}$. $^1$H NMR (90 MHz, CDCl$_3$) δ10.70 (bs, 1H, exch D$_2$O), 4.45 (q, 2H, J=4.5 Hz), 1.40 (t, 3H, J=4.5 Hz).

EXAMPLE 2

Preparation of ethyl N-nitrocarbamate without CCl$_4$

Purification Step

Fuming nitric acid (583.9 g, 8.34 mol, 90%) was added dropwise to rapidly stirred acetic anhydride (1575 mL, 14.26 mol) at 0° C. under N$_2$ (The HNO$_3$ addition rate was controlled so as not to exceed a reaction temperature of 6° C.). After the acid addition was complete, the reaction solution was warmed to 25° C. (over 15 minutes) and was allowed to stir at 25° C. for 30 minutes. The solution was then cooled to 0° C. and solid ethyl carbamate (750 g, 8.33 mol, 99%) was added (in portions) over 70 minutes, so as not to exceed a reaction temperature of 10° C. After the ethyl carbamate addition was complete, the solution was allowed to stir at 0° C. for 2 hours and was allowed to warm to 25° C. over 1 hour. The volatiles were evaporated in vacuo (at 25° C.) and the residue was dried to give off-white crystals (950.2 g, 84%, mp 62°–63° C.). The IR and $^1$H NMR spectra were essentially identical to the ethyl N-nitrocarbamate produced in example 1.

EXAMPLE 3

Preparation of ammonium ethyl N-nitrocarbamate

Anhydrous NH$_3$(g) was bubbled into a stirred solution of ethyl N-nitrocarbamate (503.0 g, 3.75 mol, mp 63°–66° C.), CH$_2$Cl$_2$ (1625 mL) and dry CH$_3$OH (825 mL), precooled to 9° C. under N$_2$, until the exothermic reaction subsided (the NH$_3$ addition rate was controlled so as not to exceed a reaction temperature of 23° C.). After the NH$_3$ addition was complete, the mixture was filtered and the collected solid was dried under high vacuum (overnight) to give ammonium ethyl N-nitrocarbamate as colorless crystals (563.0 g, 99%). mp 175°–176° C. IR (KBr) 3230 (s), 3000 (m), 1725 (s) and 1685 (s), 1445 and 1395 (s), 1310 (m), 1220 (s), 1100 (S), 1030 (m) cm$^{-1}$. $^1$H NMR (90 MHz, d$_6$-DMSO) δ 7.30 (bs, 4H, exch D$_2$O), 3.90 (q, 2H, J=4.5 Hz), 1.10 (t, 3H, J=4.5 Hz).

EXAMPLE 4

Preparation of ammonium dinitramide (ADN)

A cooled (ca. 0° C.) solution of N$_2$O$_5$ (866.5 g, 1.19 mol, 14.9% in CH$_2$Cl$_2$) was added via a Teflon cannula (under N$_2$) over 40 minutes to a rapidly stirred suspension of ammonium ethyl N-nitrocarbamate (164.0 g, 1.09 mol, mp 175°–176° C.) in dry CH$_2$Cl$_2$ (1640 mL) at −48° C. under N$_2$ (the N$_2$O$_5$ addition was controlled so as not to exceed a reaction temperature of −35° C.). After the N$_2$O$_5$ solution addition was complete, brown fumes were noted over the reaction mixture and the reaction liquid had a yellow tinge. The reaction mixture was then allowed to warm to 0° C. over 30 minutes and was stirred at 0° C. for 3 hours. The mixture was cooled to −45° C. (under a N$_2$ purge), and dry NH$_3$ (g) (58 g, 3.4 mol) was bubbled into the reaction mixture. The mixture was allowed to stir for 3 hours at 25° C. while purging with N$_2$ to remove excess NH$_3$, and was then filtered. The filter cake (containing ammonium dinitramide and ammonium nitrate) was washed with $CH_2Cl_2$ (150 mL+2×50 mL) and the residual solid was allowed to stir with $CH_3CN$ (1000 mL) under $N_2$ for 16 hours at 25° C. to dissolve the ammonium dinitramide. The combined $CH_2Cl_2$ solution was evaporated and was dried to give a tan solid (79.3 g, 82%, mp 47.50°–50° C.; Aldrich Chemical Co. mp 48.5°–50° C.). The $CH_3CN$ mixture was filtered and the filter cake was washed with additional $CH_3CN$ (2×100 mL+50 mL). The filtered ammonium nitrate was dried under high vacuum to give a white solid (92.8 g, 97%). The amber $CH_3CN$ filtrates (containing ADN) were concentrated via rotary evaporation (under reduced pressure) at 25° C. to 960 mL. This caused some ADN to precipitate and this material was removed by filtration and was dried (under high vacuum) to give a light tan solid (14.8 g, mp 88°–94° C.) $CH_2Cl_2$(2 L) was added to the combined filtrate (ca. 1 L) and ADN was precipitated. Filtration and drying gave a light tan solid (97.5 g, 72%, mp 87°–105° C.; total ADN fractions isolated 112.6 g, 83%, mp 87°–105° C.). The crude solid was dissolved in ammoniated $CH_3CN$ (500 mL) and then passed through silica gel (ca. 150 g) which was treated with ammoniated $CH_3CN$. The silica gel was then washed with ammoniated $CH_3CN$ (2 L) to remove trapped ADN (until $CH_2Cl_2$ addition to filtrate fractions no longer precipitated ADN). Evaporation and drying of the light green filtrate gave ADN as an off-white solid (109.9 g, 81%, mp 89°–91.5° C.). TLC (silica gel, $CH_3CN$) showed a dark spot at $R_f$=0.80 (ADN) and a light spot at $R_f$=0.26 (ammonium nitrocarbamate). The crude ADN (109.6 g) was dissolved (with slight warming to 33° C.) in reagent grade $CH_3OH$ (200 mL) and $CH_2Cl_2$(3 L) was added dropwise to the rapidly stirred $CH_3OH$ solution (to induce ADN precipitation/crystallization). Filtration of the crystallized ADN and drying gave white crystals (103.3 g, 76%, mp 91°–92° C.). TLC (silica gel, $CH_3CN$) showed one spot at $R_f$=0.80. IR (KBr) 3150 (s), 1550 (s), 1440 (s), and 1410 (s), 1215 (s) and 1180 (s), 1035 (m), 830 (s), 730 (s) cm$^{-1}$. $^1H$ NMR (90 MHz, $d_6$-DMSO) δ 7.25 (s, exch $D_2O$).

EXAMPLE 5

Improved Preparation of ADN (kg scale)

A cooled (ca. 0° C.) solution of $N_2O_5$ (8187.2 g, 11.29 mol, 14.9% in $CH_2Cl_2$) was added via a Teflon cannula (under $N_2$) over 13 minutes to a rapidly stirred suspension of ammonium ethyl N-nitrocarbamate (1550.9 g, 10.3 mol, mp 175°–176° C.) in dry $CH_2Cl_2$ (10.3 L) at −51° C. under $N_2$ (the $N_2O_5$ addition was controlled so as not to exceed a reaction temperature of −35° C.). The reaction mixture was warmed to 0° C. over about 1 hour and was stirred at 0° C. for a total 3.5 hours. The mixture was cooled to −45° C. (under a $N_2$ purge), and dry $NH_3$ gas (385.6 g, 22.68 mol) was bubbled into the reaction mixture at such a rate so as not to exceed a reaction temperature of −34° C. (final pH of solution was ca. 8). The mixture was stirred for 12 hours (after the $NH_3$ addition was complete), during which time it was allowed to warm to 13° C., and was filtered. The filter cake (containing ADN and AN) was washed with $CH_2Cl_2$ (2×1.5 L) and the filtered solid was then allowed to stir with $CH_3CN$ (8 L) under $N_2$ for 16 hours at 25° C. to dissolve-out ADN. More ADN is recoverable by additional acetonitrile extractions. The $CH_3CN$ mixture was filtered and the filter cake was triturated with additional $CH_3CN$ (2×2 L). The amber $CH_3CN$ filtrates (containing ADN) were concentrated via rotary evaporation (under reduced pressure) at 25° C. to ca. 3 L and purged with ammonia (for ca. 1 min) to dissolve precipitated solids. The concentrated ADN/$CH_3CN$ solution was then passed through silica gel (ca. 1 kg) which has been treated with ammoniated $CH_3CN$. The silica gel was washed with ammoniated $CH_3CN$ (ca. 7 L) to remove trapped ADN. The combined filtrate was evaporated and the residual light tan solid was dissolved (with slight warming to 27° C.) in reagent grade $CH_3OH$ (1.40 L) and $CH_2Cl_2$ (19 L) was added via a cannula to the rapidly stirred solution (to induce ADN precipitation/crystallization). After the $CH_2Cl_2$ addition was complete, the mixture was cooled to 0° C. and was allowed to stir for 18 hours at that temperature. Filtration of the crystallized ADN, followed by trituration of the filter cake with $CH_2Cl_2$ (ca. 4 L), and drying gave white crystals (931 g, 73%, mp 90°–93° C.). TLC (silica gel, $CH_3CN$) showed one spot at $R_f$=0.80. The IR and $^1H$ NMR spectra were identical in all essential respects to authentic ADN prepared previously.

Numerous other modifications and variations of the present invention are possible in light of the foregoing teachings. It is therefore to be understood that within the scope of the appended claims the invention may be practiced otherwise than as specifically described.

What is claimed is:

1. A process for producing ammonium dinitramide comprising the following steps in order:

(1) nitrating a compound of the formula Z—$NH_2$ to form a compound of the formula Z—$NHNO_2$;

(2) reacting the compound Z—$NHNO_2$ with ammonia under anhydrous conditions to produce a salt of the formula Z—$NNO_2^-NH_4^+$;

(3) nitrating the salt Z—$NNO_2^-NH_4^+$ and then treating the reaction mixture with ammonia to produce ammonium dinitramide, ammonium nitrate, and regenerate the compound Z—$NH_2$, and (4) isolating the product ammonium dinitramide;

wherein Z is —$COOCH_2CH_3$, or —$COOCH_3$.

2. The process of claim 1 wherein Z—$NH_2$ is ethyl carbamate, $CH_3CH_2OOCNH_2$.

3. The process of claim 1 wherein Z—$NH_2$ is methyl carbamate, $CH_3OOCNH_2$.

4. The process of claim 1 wherein ammonium nitrate is isolated as a product after step (3).

5. The process of claim 1 wherein the regenerated Z—$NH_2$ compound is recovered after step (3) for reuse in the process.

6. The process of step 1 wherein acetyl nitrate is used to nitrate the Z—$NH_2$ compound in step (1).

7. The process of claim 1 wherein the nitrating agent used in step (3) to nitrate the salt Z—$NO_2^-NH_4$ is nitrogen pentoxide or nitronium tetrafluoroborate.

8. The process of claim 7 wherein the nitrating agent used in step (5) is nitrogen pentoxide.

* * * * *